United States Patent
Hsiao

(10) Patent No.: US 9,849,206 B1
(45) Date of Patent: Dec. 26, 2017

(54) LIQUID PERFUME DIFFUSER

(71) Applicant: Ming Jen Hsiao, Miaoli County (TW)

(72) Inventor: Ming Jen Hsiao, Miaoli County (TW)

(*) Notice: Subject to any disclaimer, the term of this patent is extended or adjusted under 35 U.S.C. 154(b) by 0 days.

(21) Appl. No.: 15/362,273

(22) Filed: Nov. 28, 2016

(51) Int. Cl.
*A61L 9/12* (2006.01)
*B65D 1/02* (2006.01)

(52) U.S. Cl.
CPC ............ *A61L 9/127* (2013.01); *B65D 1/0246* (2013.01)

(58) Field of Classification Search
CPC .......... A61L 9/12; A61L 9/127; B65D 1/0246
See application file for complete search history.

(56) References Cited

U.S. PATENT DOCUMENTS

| | | | |
|---|---|---|---|
| 4,323,193 A * | 4/1982 | Compton | A61L 9/127 239/44 |
| 4,731,520 A | 3/1988 | Glucksman et al. | |
| 5,449,117 A | 9/1995 | Muderlak et al. | |
| 9,480,769 B2 | 11/2016 | Sevy | |
| 2010/0176211 A1* | 7/2010 | Bulsink | A61L 9/127 239/44 |

* cited by examiner

*Primary Examiner* — Christopher Kim
(74) *Attorney, Agent, or Firm* — Ming Chow; Sinorica, LLC

(57) ABSTRACT

A liquid perfume diffuser includes a perfume bottle holding a liquid perfume, an inner cap threaded onto the perfume bottle, a rotary cover rotatably capped on the inner cap for pressing and rotating by the user to move the inner cap relative to the perfume bottle between a close position and an open position, so that when the perfume is opened, the liquid perfume can then be absorbed by a liquid-absorbing material in the rotary cap, enabling the pleasant smell of the liquid perfume to be slowly and naturally released into the outside open air through a capillary effect.

11 Claims, 11 Drawing Sheets

LIQUID PERFUME DIFFUSER

1. FIELD OF THE INVENTION

The present invention relates to scent releasing devices and more specifically, to a liquid perfume diffuser, which has a special structural design that allows the user to control the evaporation of the liquid perfume into the outside open air only when desired and that prohibits a child from improperly using the liquid perfume diffuser to cause leakage of the liquid perfume out of the perfume bottle through the inner cap, thereby prolonging the application time and avoiding wasting the liquid perfume.

2. DESCRIPTION OF THE RELATED ART

A perfume diffuser, for example, an inverted perfume diffuser, generally comprises a liquid perfume container holding a liquid perfume, a bottleneck located at a bottom side of the liquid perfume container, a cap capped on the bottleneck, a tapered liquid guide hole located in the bottom side of the cap, a hollow base for holding the liquid perfume container on a flat surface in such a manner that the bottleneck suspends inside the hollow base, a liquid-absorbing material placed in the hollow base and kept in contact with the liquid guide hole. The hollow base comprises a plurality of through holes cut through the peripheral wall. Thus, the liquid perfume can flow out of the liquid guide hole and then be absorbed by the liquid-absorbing material for evaporation into the outside open air through the through holes of the hollow base. However, because the liquid perfume container is supported on the hollow base in an upside-down position, the liquid-absorbing material can be over-wetted. Thus, the liquid perfume diffusing amount cannot be properly controlled, leading to waste of the liquid perfume. Too rich aroma can destroy the atmosphere. Further, the inverted perfume diffuser can fall down accidentally, leading in to an environmental pollution or security problem.

When using a natural volatile aromatic device, the user can open the inner cap of the container for enabling the contained liquid perfume to be evaporated into the outside open air continuously. As the liquid perfume is being continuously evaporated into the air, the user cannot control the diffusing amount of the liquid perfume. Some other designs use a liquid-absorbing material for absorbing the contained liquid perfume from the liquid perfume container through a cotton rope for evaporation into the air. However, when the level of the liquid perfume in the liquid perfume container is lowered to a certain extent, the speed in delivering the liquid perfume from the liquid perfume container through the cotton rope to the liquid-absorbing material will be slowed down, affecting the liquid perfume diffusing performance.

SUMMARY OF THE INVENTION

The present invention has been accomplished under the circumstances in view. It is therefore an object of the present invention to provide a liquid perfume diffuser, which allows the user to control the evaporation of the liquid perfume into the outside open air only when desired, prolonging the application time and avoiding wasting the liquid perfume.

It is another object of the present invention to provide a liquid perfume diffuser, which prevents the liquid perfume from leakage due to an improper operation to remove the perfume bottle from the inner cap or when the liquid perfume diffuser is placed lying down or being moved.

It is still another object of the present invention to provide a liquid perfume diffuser, which facilitates carrying and application.

To achieve these and other objects of the present invention, a liquid perfume diffuser comprises a perfume bottle, an inner cap, a rotary cover, and a liquid-absorbing material. The perfume bottle holds a liquid perfume therein, comprising a bottleneck located at a top side thereof, a male thread extended around the periphery of the bottleneck, and a bottle stopper fastened to the bottleneck. The bottle stopper comprises a liquid guide tube extended through opposing top and bottom ends thereof, and a fine pore located in a closed bottom end of the liquid guide tube in communication with an opposing top open end of the guide tube. The inner cap comprises a bottom opening, a top cap head, a protruding tube, a female thread and a plurality of protruding blocks. The protruding tube is axially located at the center of the top cap head, comprising a bottom wall that suspends inside the inner cap and blocks up a bottom end of the protruding tube, a plug downwardly extended from the bottom wall, and a liquid guide hole cut through the bottom wall in communication with the inside space of the protruding tube. The protruding blocks are located at a top side of the top cap head, and spaced around the protruding tube. The female thread is located on an inside wall of the inner cap for rotatably receiving the male thread of the perfume bottle for enabling the plug to be press-fitted into the liquid guide tube to seal the liquid guide tube and the liquid guide hole. The rotary cover is a hollow cylindrical shell member, comprising an inner race and a plurality of notches. The inner race comprises an opening at a free end thereof. The notches are spaced around the opening of the inner race. The rotary cover is rotatably capped on the inner cap to attach the inner race onto the protruding tube, and to force the notches into abutment against the respective protruding blocks at a top side. The liquid-absorbing material is mounted in the inner race of the rotary cover in contact with a top side of the protruding tube of the inner cap for absorbing the liquid perfume.

Thus, when using the perfume diffuser, the user can hold the perfume bottle with one hand, and then press the rotary cover and simultaneously rotate the rotary cover with the other hand to move the free end of the inner race over the top edges of the protruding blocks of the inner cap and to further force the respective notches into engagement with the respective protruding blocks. When the user continuously rotate the rotary cover after engagement between the notches and the respective protruding blocks, the inner cap is rotated with the rotary cover to carry the female thread in direction away from the male thread of the perfume bottle and to pull the plug in direction away from the liquid guide tube, allowing air and liquid communication in between the inside space of the perfume bottle, the fine pore, the inside space of the liquid guide tube, the liquid guide hole and the inside space of the protruding tube. At this time, the user can shake the perfume bottle to force the liquid perfume out of the perfume bottle through the fine pore, the liquid guide tube, the liquid guide hole of the protruding tube toward the liquid-absorbing material, enabling the liquid perfume to be absorbed by the liquid-absorbing material so that the perfume molecules can then be diffused into the surrounding environment subject to the capillary effects of the liquid-absorbing material that is disposed in contact with the outside open air.

When compared to conventional designs, the liquid perfume diffuser of the present invention allows the user to control the evaporation of the liquid perfume into the outside open air only when desired, prolonging the application time and avoiding wasting the liquid perfume. Further, the structural design of the present invention can prohibit a child from improperly using the liquid perfume diffuser to cause leakage of the liquid perfume out of the perfume bottle through the inner cap. Further, the liquid perfume diffuser of the present invention facilitates carriage and application.

Other advantages and features of the present invention will be fully understood by reference to the following specification in conjunction with the accompanying drawings, in which like reference signs denote like components of structure.

DETAILED DESCRIPTION OF THE PREFERRED EMBODIMENT

Figure 1:
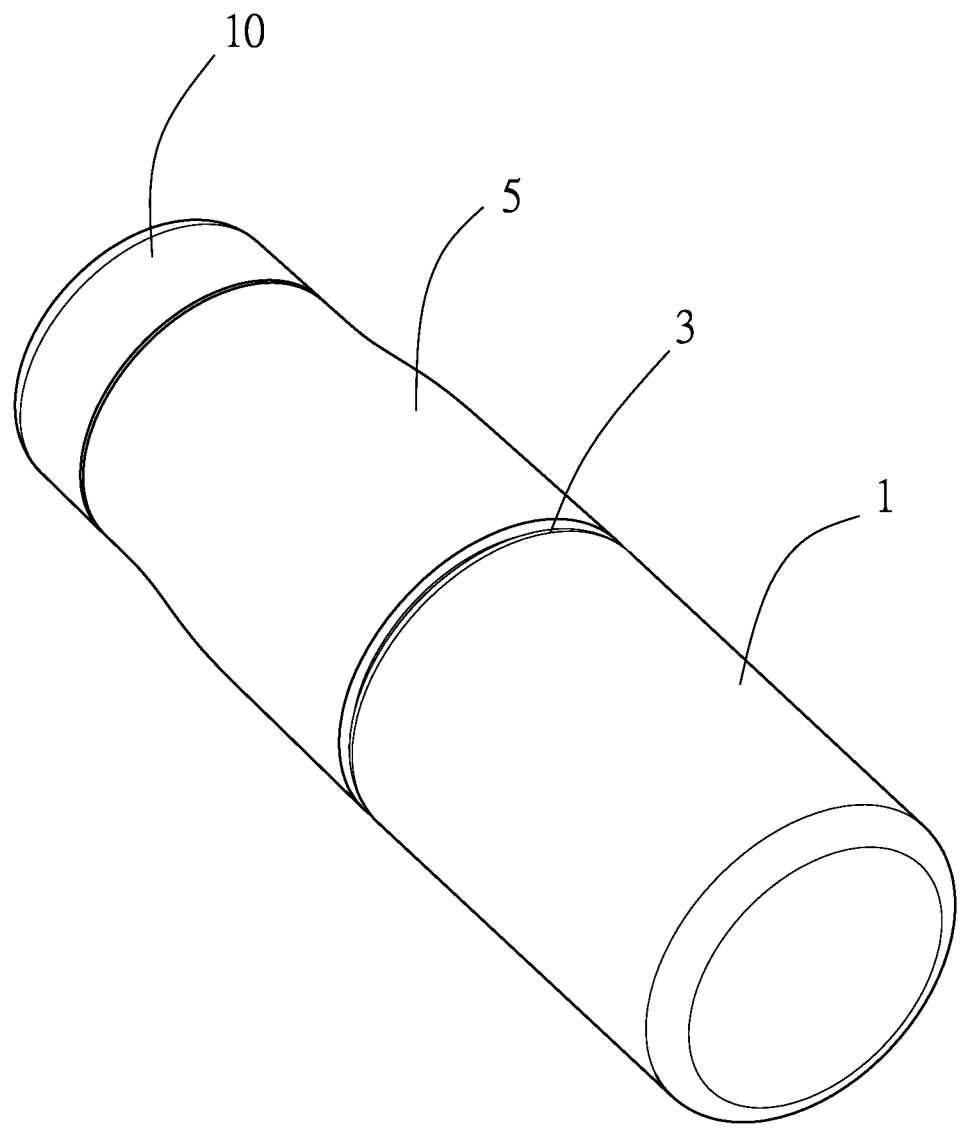
FIG. 1 is an elevational view of a liquid perfume diffuser in accordance with the present invention.

Referring to FIGS. 1-8, a liquid perfume diffuser 1 in accordance with the present invention is shown. The liquid perfume diffuser comprises a perfume bottle 1 holding a liquid perfume, an inner cap 3, a rotary cover 5, and a liquid-absorbing material 7.

The perfume bottle 1 comprises a bottleneck 11 located at a top side thereof, a male thread 13 spirally extended around the periphery of the bottleneck 11, and a bottle stopper 15 fastened to the bottleneck 11. The bottle stopper 15 comprises a liquid guide tube 151 extended through opposing top and bottom ends thereof, and a fine pore 153 located in a closed bottom end of the liquid guide tube 151 in communication with an opposing top open end of the liquid guide tube 151 and facing toward the inside of the perfume bottle 1.

The inner cap 3 comprises a bottom opening 31, a top cap head 33, a protruding tube 35, a female thread 37, and a plurality of protruding block 39. The protruding tube 35 is axially located at the center of the top cap head 33, comprising a bottom wall 351 that suspends inside the inner cap 3 and blocks up a bottom end of the protruding tube 35, a plug 353 downwardly extended from the bottom wall 351, a liquid guide hole 355 cut through the bottom wall 351 in communication with the inside space of the protruding tube 35. The protruding blocks 39 are located at a top side of the top cap head 33 and spaced around the protruding tube 35. The female thread 37 is located on an inside wall of the inner cap 3. The male thread 13 of the perfume bottle 1 is rotatably threaded into engagement with the female thread 37 to press-fit the plug 353 into the liquid guide tube 151, thereby sealing the liquid guide tube 151 and the liquid guide hole 355.

The rotary cover 5 is a hollow cylindrical shell member, comprising an inner race 51 and a plurality of notches 55 spaced around the opening 53 at the free end of the inner race 51. The rotary cover 5 is rotatably capped on the inner cap 3 to attach the inner race 51 to the outer perimeter of the protruding tube 35 and to force the notches 55 into abutment against the respective protruding blocks 39 at the top side.

The liquid-absorbing material 7 is mounted in the inner race 51 of the rotary cover 5 in contact with the top end of the protruding tube 35 of the inner cap 3. Further, the liquid-absorbing material 7 can be selected from the group of sponge, cotton, non-woven fabric and porous ceramics that have siphon capillary characteristics.

Referring to FIGS. 6-8 again, when using the perfume diffuser, the user can hold the perfume bottle 1 with one hand, and then press the rotary cover 5 and simultaneously rotate the rotary cover 5 in the clockwise direction with the other hand to move the free end of the inner race 51 over the top edges of the protruding blocks 39 of the inner cap 3 and to further force the respective notches 55 into engagement with the respective protruding blocks 39. When the user continuously rotate the rotary cover 5 after engagement between the notches 55 and the respective protruding blocks 39, the inner cap 3 is rotated with the rotary cover 5 to carry the female thread 37 in direction away from the male thread 13 of the perfume bottle 1 and to pull the plug 353 in direction away from the liquid guide tube 151, allowing air and liquid communication in between the inside space of the perfume bottle 1, the fine pore 153, the inside space of the liquid guide tube 151, the liquid guide hole 355 and the inside space of the protruding tube 331. At this time, the user can shake the perfume bottle 1 to force the liquid perfume out of the perfume bottle 1 through the fine pore 153, the liquid guide tube 151, the liquid guide hole 355 of the protruding tube 35 toward the liquid-absorbing material 7, enabling the liquid perfume to be absorbed by the liquid-absorbing material 7 so that the perfume molecules can then be diffused into the surrounding environment subject to the capillary effects of the liquid-absorbing material 7 that is disposed in contact with the outside open air.

On the contrary, the user can hold the perfume bottle 1 with the one hand and press and rotate the rotary cover 5 in the counter-clockwise direction with the other hand to move the free end of the inner race 51 over the top edges of the protruding blocks 39 of the inner cap 3 and to further force the respective notches 55 into engagement with the respective protruding blocks 39. When the user continuously rotate the rotary cover 5 counter-clockwise after engagement between the notches 55 and the respective protruding blocks 39, the inner cap 3 is rotated with the rotary cover 5 to carry the female thread 37 in direction toward the rear end of the male thread 13 of the perfume bottle 1 and to force the plug 353 into the liquid guide tube 151, thereby sealing the fine pore 153 and liquid guide tube 151 of the bottle stopper 15 of the perfume bottle 1, the liquid guide hole 355 and the inside space of the protruding tube 331. Sealing the perfume bottle 1, the liquid guide hole 355 and the inside space of the protruding tube 331 prevents the liquid-absorbing material 7 from absorbing an excessive amount of the liquid perfume due to oscillation of the liquid perfume diffuser during movement, or uninterruptedly evaporation of the liquid perfume due to constant contact with the outside air.

If the user releases the downward pressure from the rotary cover 5, the notches 55 will be moved upward and disengaged from the respective protruding blocks 39, thus, rotating the rotary cover 5 relative to the inner cap 3 will run idle without moving inner cap 3 toward or away from the perfume bottle 1.

The liquid perfume diffuser of the present invention has other advantages. The application method of the invention is to shake the perfume bottle 1. By means of the fine pore 153 to control the flow rate, the liquid perfume will not be instantaneously excessively introduced into the liquid guide tube 151 and the liquid guide hole 355 and the liquid-absorbing material 7 will not instantaneously absorb an excessive amount of the liquid perfume, avoiding perfume overflow. When the liquid perfume diffuser is placed lying down or being moved after sealed the perfume bottle 1, the liquid perfume will not be absorbed by the liquid-absorbing material 7, avoiding waste of use or leakage of the liquid perfume; in application, the user needs to press and rotate the rotary cover 5, driving the inner cap 3 to move the plug 353 backwardly away from the liquid guide tube 151 of the perfume bottle 1, thereby opening the fine pore 153 and liquid guide tube 151 of the bottle stopper 15 of the perfume bottle 1 for direct communication with the liquid guide hole 355, and thus, the user can operate the liquid perfume diffuser for enabling the liquid-absorbing material 7 to absorb the liquid perfume when needed, maintaining a longer use of time. The structural design of the present invention can prohibit a child from improperly using the liquid perfume diffuser to cause leakage of the liquid perfume out of the perfume bottle 1 through the inner cap 3. Further, the liquid perfume diffuser of the present invention facilitates carriage and application.

Referring to FIGS. 4A, 4B, 5A, 5B and 5C, each protruding block 39 of the inner cap 3 has a beveled surface 391; the rotary cover 5 further comprises a beveled edge 551 located at one side of each notch 55 of the inner race 51 to mate with one respective beveled surface 391. Thus, when the user presses the rotary cover 5 and then rotates the rotary cover 5, the respective beveled edges 551 of the inner race 51 are respectively slidably kept in contact with the respective beveled surfaces 391 of the protruding block 39, guiding the notches 55 into positive engagement with the respective protruding blocks 39 for enabling the inner cap 3 to be rotated with the rotary cover 5 relative to the perfume bottle 1.

In the present preferred embodiment, the liquid guide tube 151 is an inverted cone tube; the plug 353 is cone plug.

Preferably, the inner cap 3 further comprises a stop ring 32 extended around the outer perimeter thereof; the rotary cover 5 further comprises an inner annular flange 52 extended around an inside wall thereof below the inner race 51 and stopped at a bottom side of the stop ring 32 of the inner cap 3 to prevent escaping of the rotary cover 5 out of the inner cap 3.

The inner annular flange 52 defines a beveled surface portion 521 sloping downwardly inwards toward the inside wall of the rotary cover 5; the inner cap 3 further comprises a tapered sliding wall 34 downwardly outwardly extended from a bottom side thereof. Thus, when the rotary cover 5 is forced downward or moves upward relative to the inner cap 3, the beveled surface portion 521 of the inner annular flange 52 is moved over the outer surface of the tapered sliding wall 34 (a predetermined distance), forcing the notches 55 into engagement with the respective protruding blocks 39 or moving the notches 55 away from the respective protruding blocks 39.

During the operation or use of the liquid perfume diffuser, a small amount of the liquid perfume molecules can flow downwards and stopped by the male thread 13 and the female thread 37 to leak out of the perfume bottle 1. In order to eliminate this problem, the inner cap 3 is configured to provide a tooth ring 36 extended around the inside wall thereof below the female thread 37 for abutment against the periphery of the perfume bottle 1 below the male thread 13. The tooth ring 36 comprises a plurality of tooth claws 361 equiangularly spaced around the inside wall of the inner cap 3, and a the gap 363 defined between each two adjacent tooth claws 361 for accumulating liquid perfume molecules that leak out of the perfume bottle 1 during the operation or use of the liquid perfume diffuser.

Figure 2:
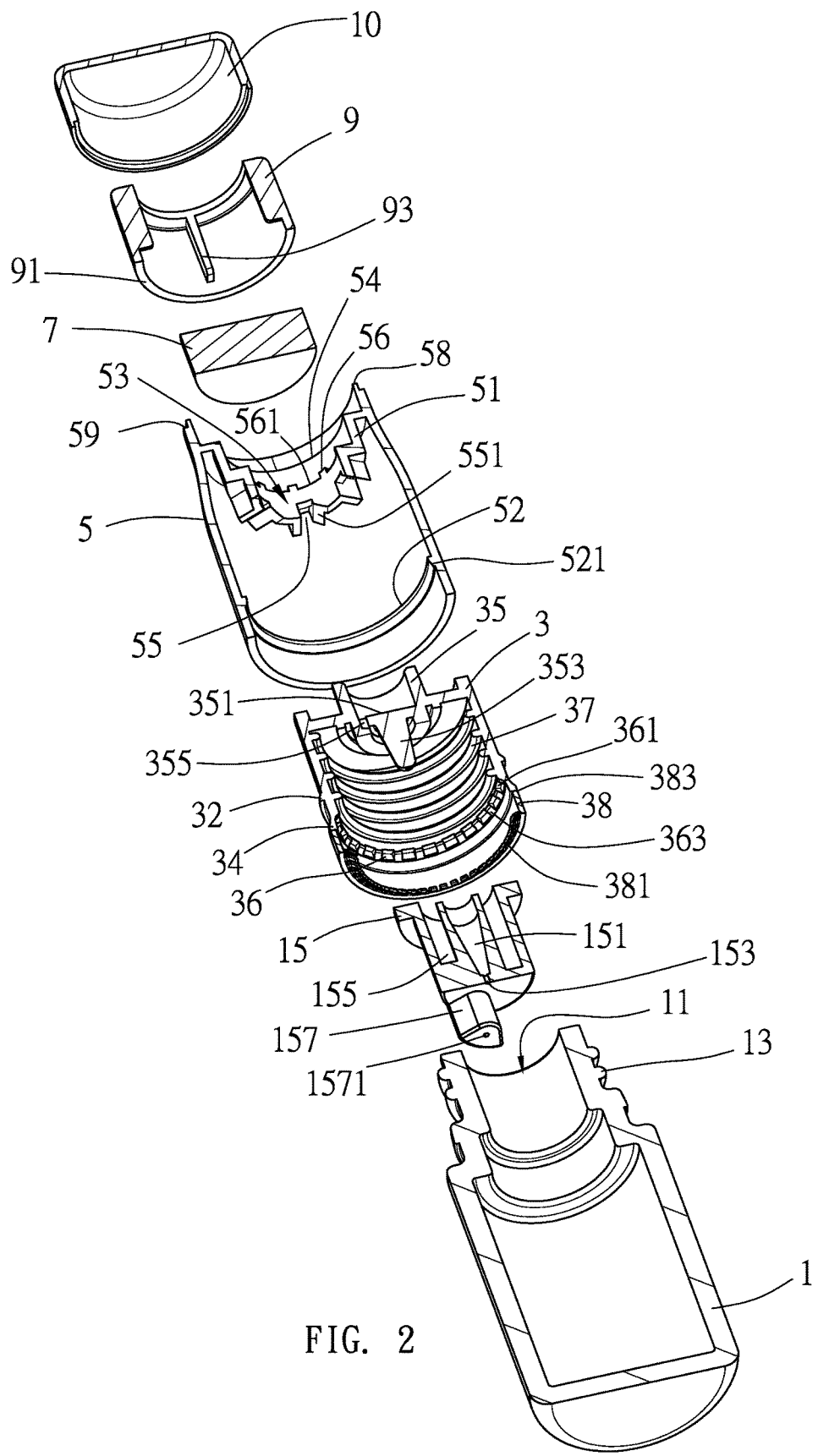
FIG. 2 is an exploded sectional elevational view of the liquid perfume diffuser in accordance with the present invention.
Figure 3:
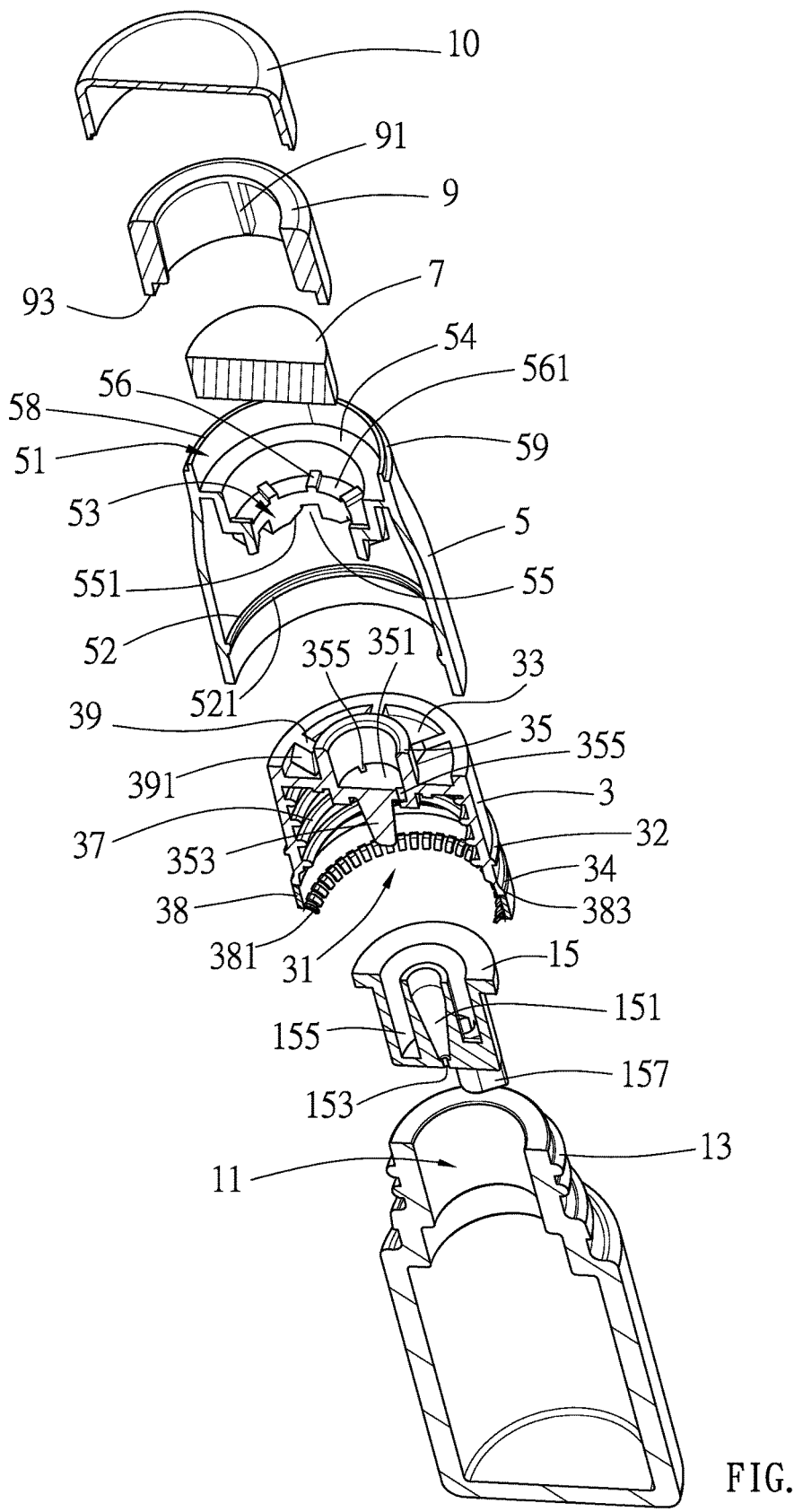
FIG. 3 is another exploded sectional elevational view of the liquid perfume diffuser in accordance with the present invention.
Figure 4A:
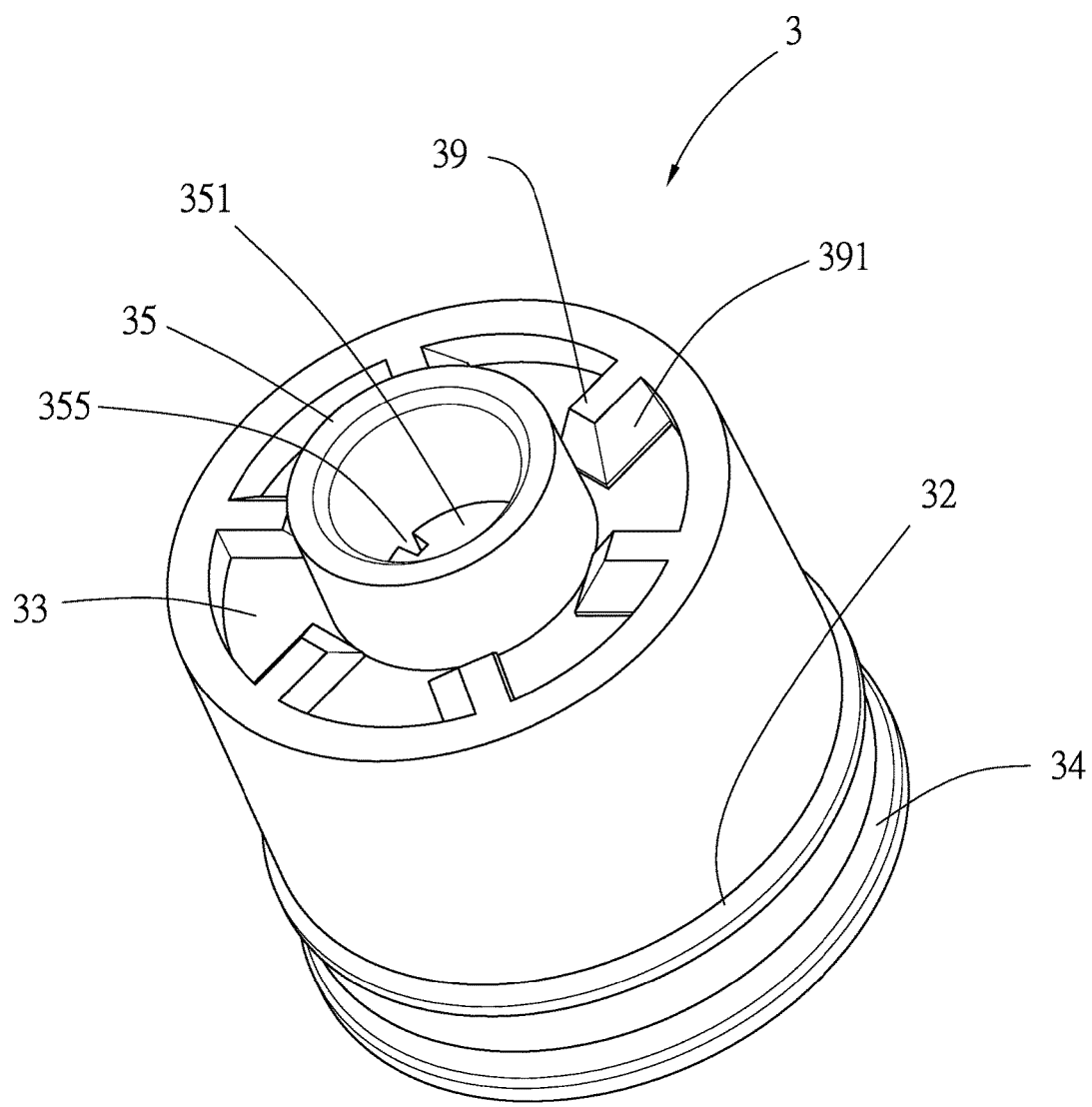
FIG. 4A is an oblique top elevational view, in an enlarged scale, of the inner cap of the liquid perfume diffuser in accordance with the present invention.
Figure 4B:
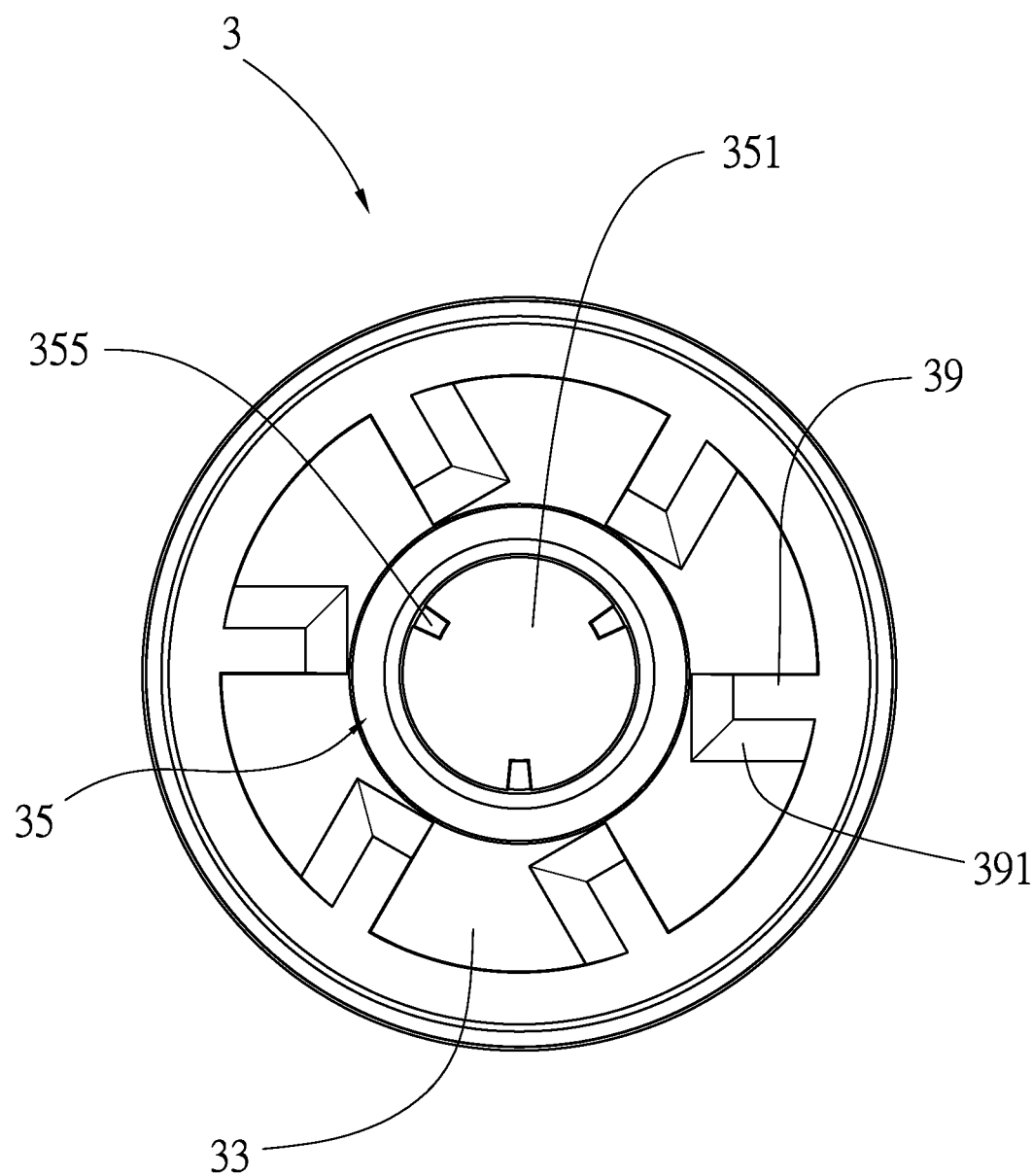
FIG. 4B is a schematic top view of the inner cap shown in FIG. 4A.
Figure 5A:
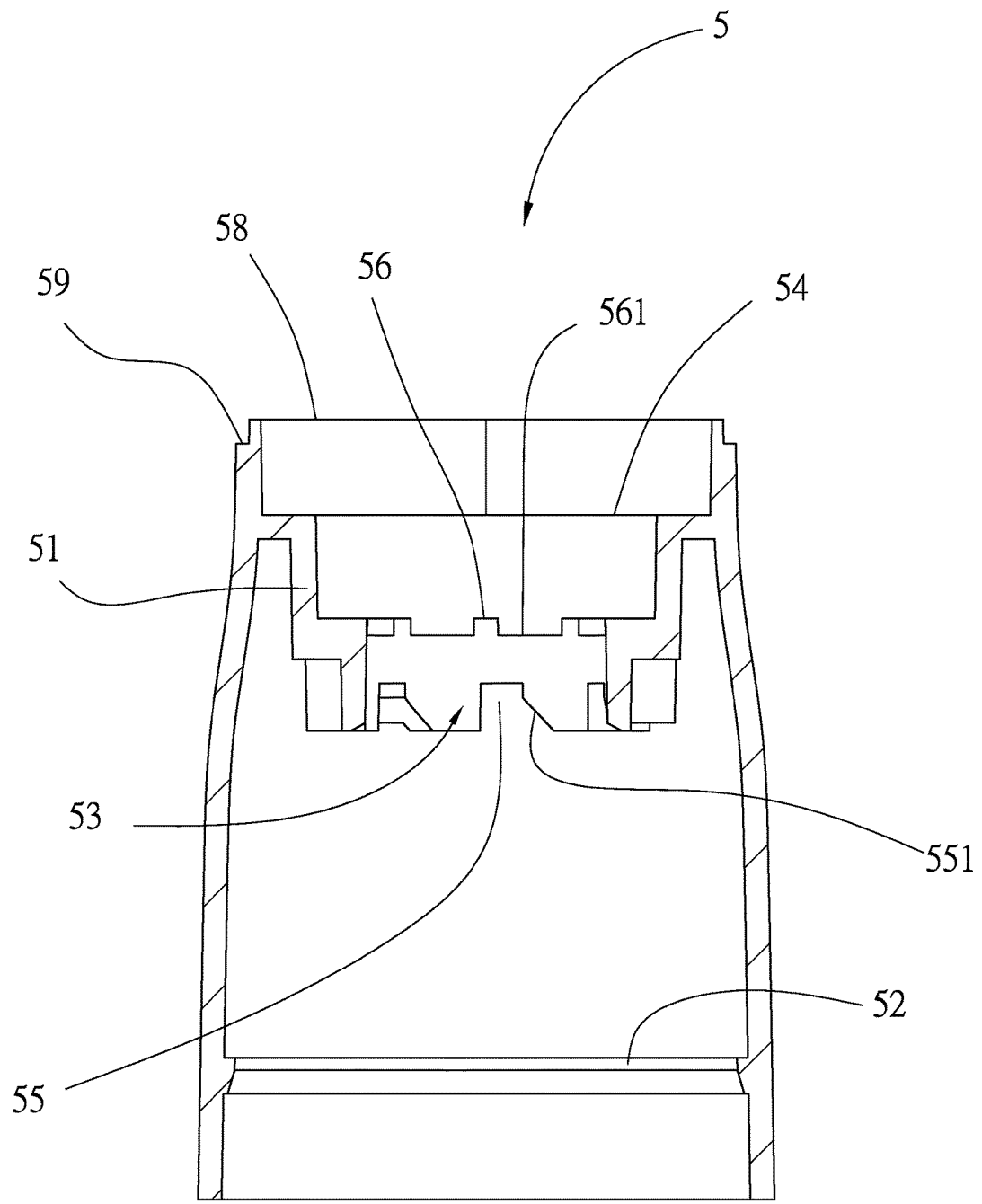
FIG. 5A is a longitudinal sectional view of the inner cap shown in FIG. 4A.
Figure 5B:
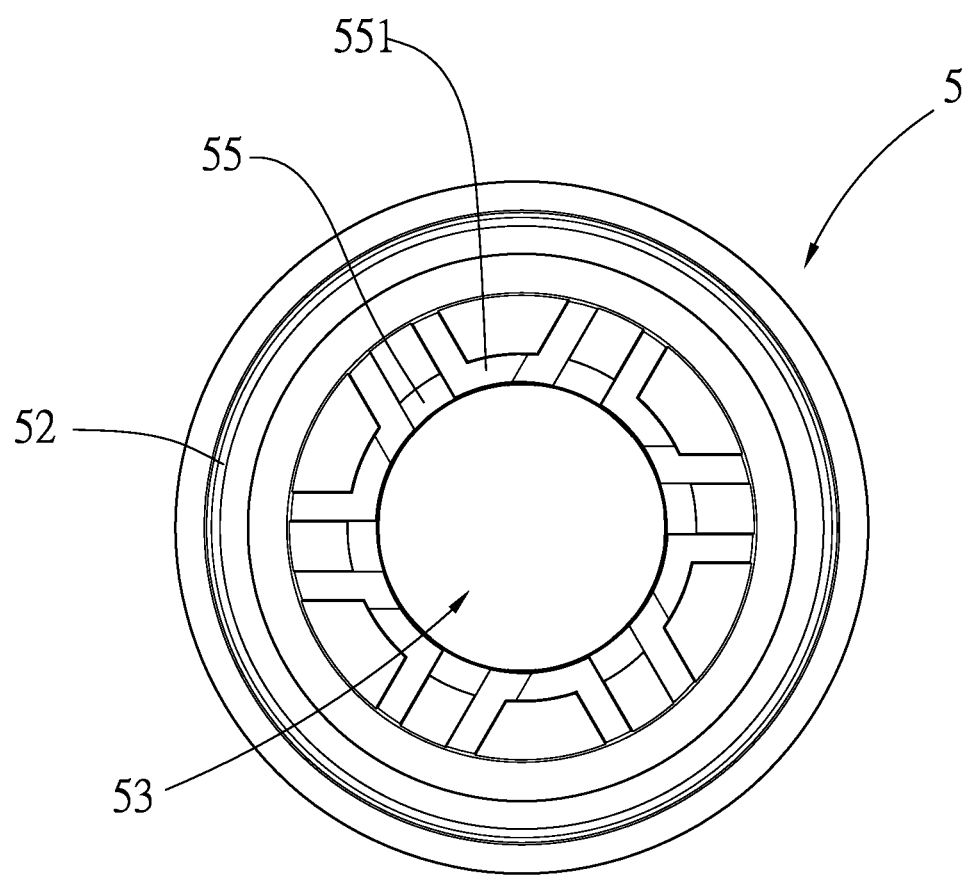
FIG. 5B is a schematic bottom view of the inner cap shown in FIG. 4A.
Figure 5C:
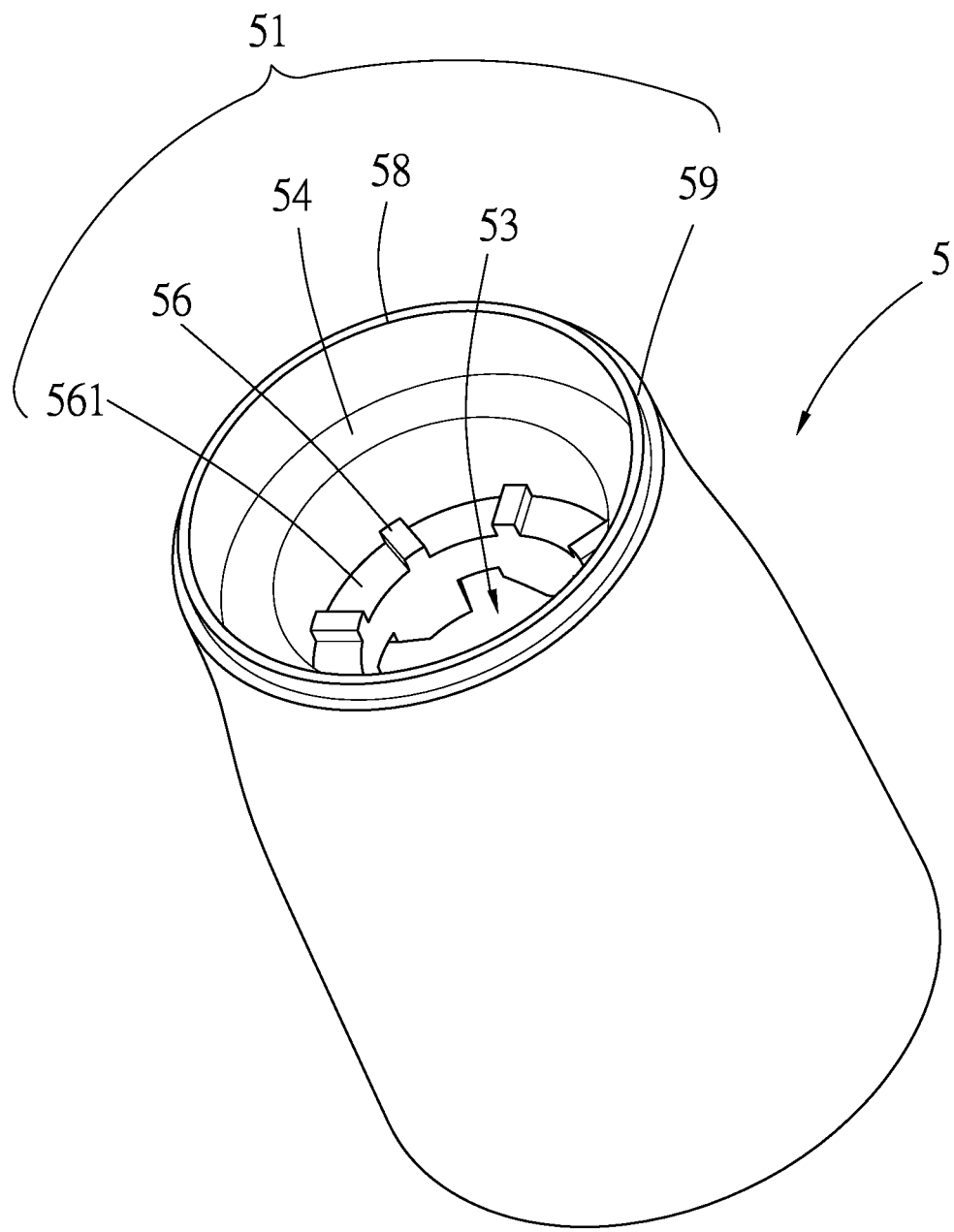
FIG. 5C is an oblique top elevational view, in an enlarged scale, of the rotary cap of the liquid perfume diffuser in accordance with the present invention.
Figure 6:
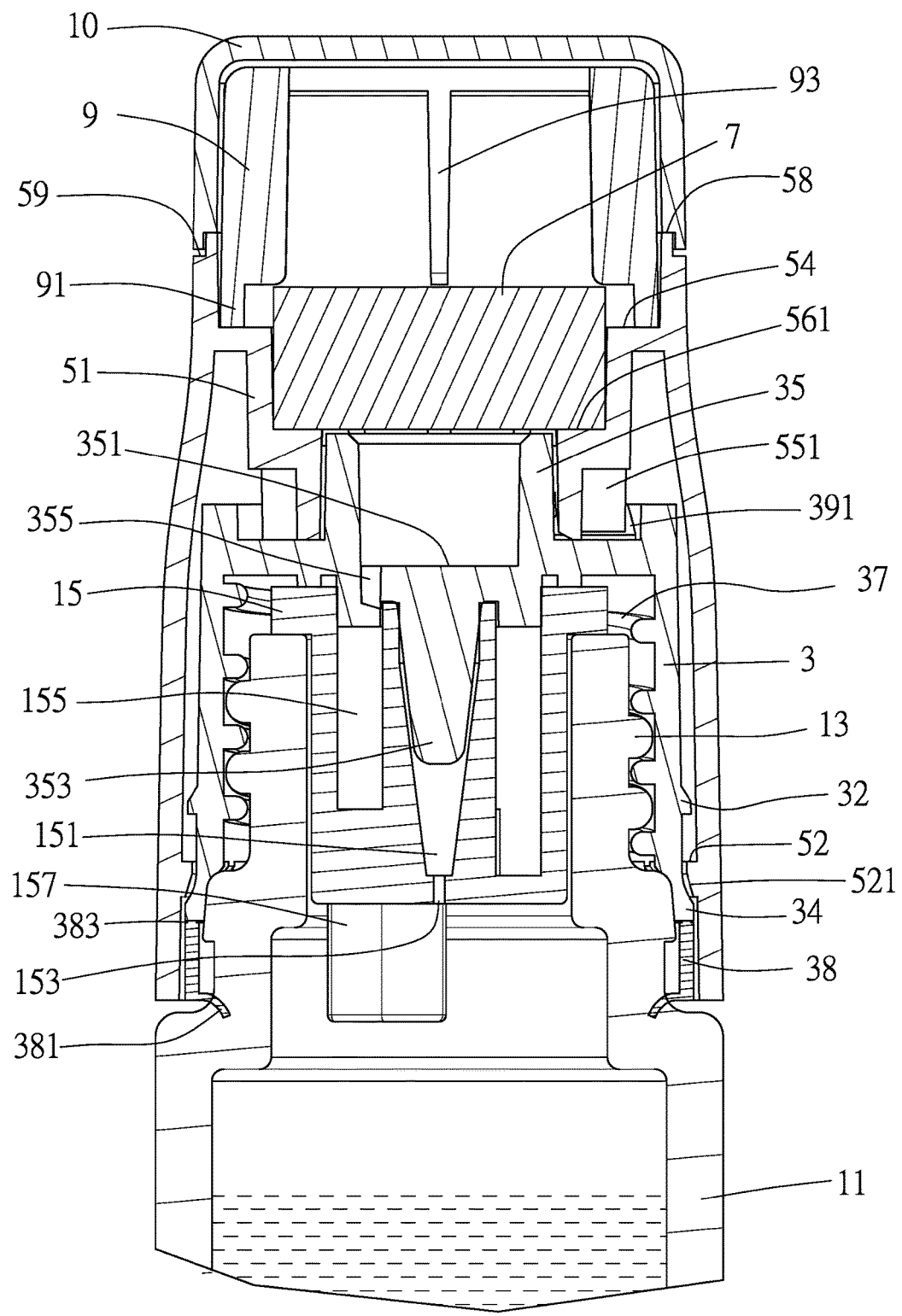
FIG. 6 is a schematic sectional assembly view, in an enlarged scale, of a part of the liquid perfume diffuser in accordance with the present invention.
Figure 7:
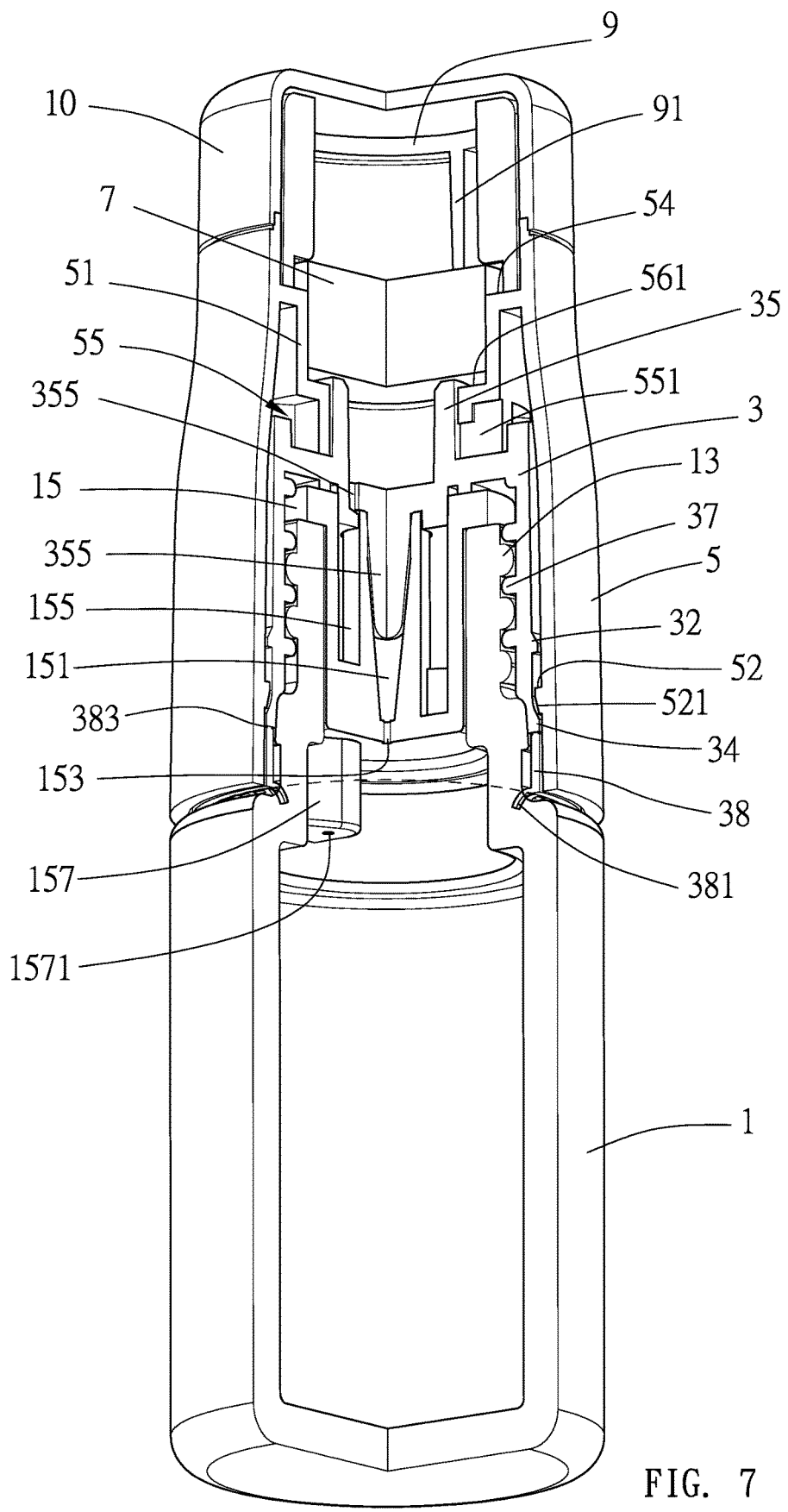
FIG. 7 is a sectional elevational view, in an enlarged scale, of the liquid perfume diffuser in accordance with the present invention.
Figure 8:
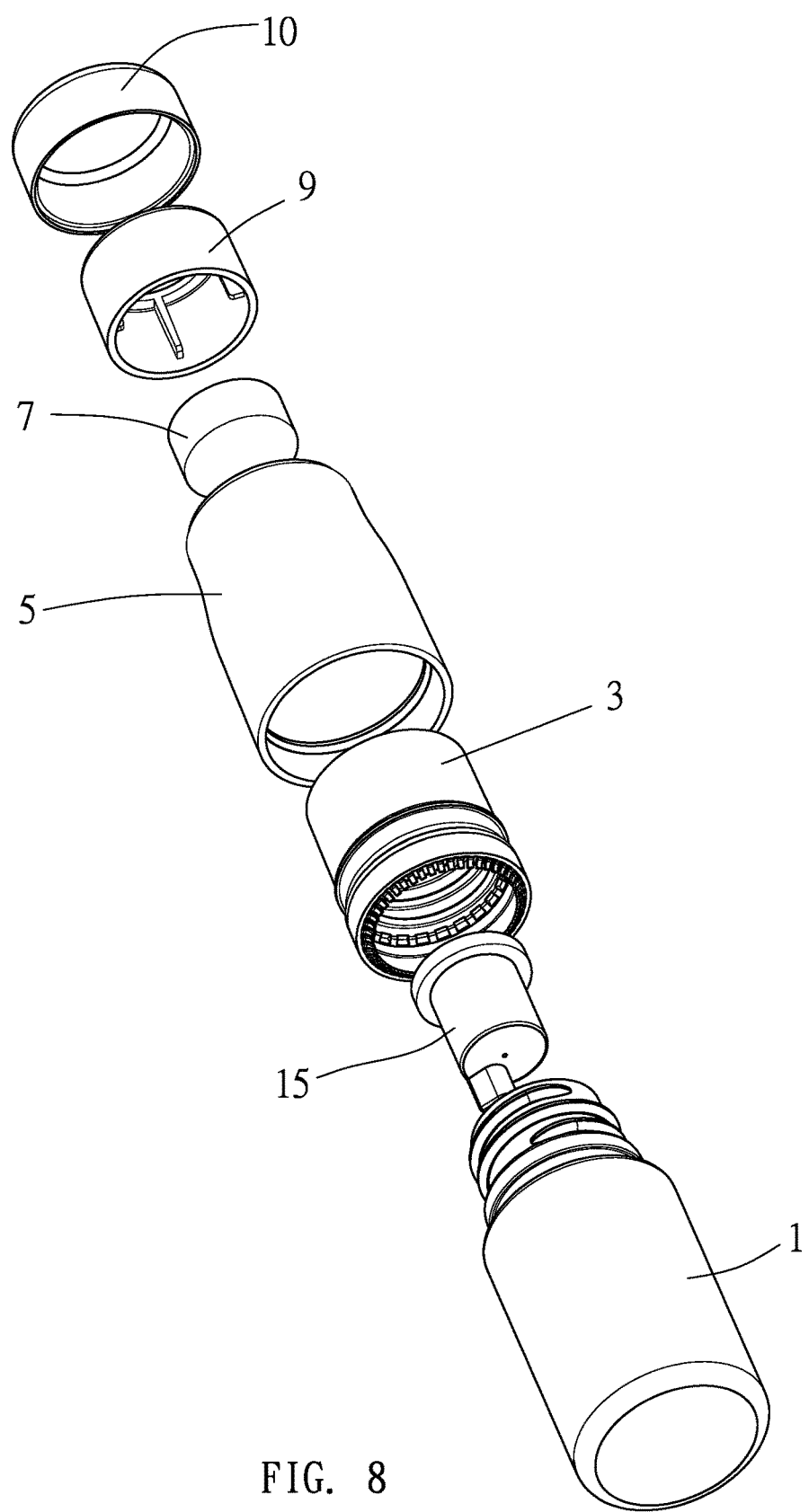
FIG. 8 is an exploded view of the liquid perfume diffuser in accordance with the present invention.

Referring to FIGS. 2, 3 and 7, the inner cap 3 further comprises a sealing ring 38 sealed to a bottom edge of the tapered sliding wall 34. The sealing ring 38 has a top edge thereof bonded to the bottom edge of the tapered sliding wall 34 by ultrasonic sealing technology to form a tear line 383 between the tapered sliding wall 34 and the sealing ring 38, and a plurality of claw portions 381 equiangularly space around an opposing bottom edge thereof. When the female thread 37 of the inner cap 3 is threaded into engagement with the male thread 13 of the perfume bottle 1, the claw portions 381 of the sealing ring 38 are hooked on a bottom side of the male thread 13 of the perfume bottle 1. When the user uses the liquid perfume diffuser at the first time, press the rotary cover 5 to force the notches 55 into engagement with the respective protruding blocks 39 of the inner cap 3, and then rotate the rotary cover 5 in the reversed direction to move the female thread 37 in direction away from the male thread 13 of the perfume bottle 1 for a small distance. At the moment when the rotation operation is started, the tear line 383 of the sealing ring 38 will be broken and separated from the inner cap 3, leaving the sealing ring 38 at the bottleneck 11. At the time when the tear line 383 of the sealing ring 38 is broken and separated from inner cap 3, a tactile or visual message is given to the user, enabling the user to know that the liquid perfume diffuser has been opened like the first time your open the bottle cap of a bottle beverage.

Referring to FIGS. 2, 3, 6, 7 and 8, the inner race 51 of the rotary cover 5 further comprises a first inner step 54 and a second inner step 56. The first inner step 54 extends around an inside wall of the inner race 51 at a top side. The second inner step 56 is concentrically spaced below the first inner step 54 and defines an inner diameter relatively smaller than the inner diameter of the first inner step 54. The opening 53 of the inner race 51 is surrounded by a bottom side of the second inner step 56. The inner race 51 further comprises a plurality of grooves 561 located on the second inner step 56. If the liquid-absorbing material 7 absorbs an excessive amount of the liquid perfume, the liquid-absorbing material 7 can release the excessive amount of the liquid perfume into the grooves 561 for storage temporarily. After evaporation of a part of the liquid perfume from the liquid-absorbing material 7, the liquid-absorbing material 7 can then absorb the temporarily accumulated liquid perfume from the grooves 561. The liquid perfume diffuser further comprises a ring cap 9. The ring cap 9 comprises a bottom edge 91 stopped at the first inner step 54 of the inner race 51, and a plurality of axial ribs 93 equiangularly spaced around an inside wall thereof above the bottom edge 91 and stopped at a top side of the liquid-absorbing material 7 to hold down the liquid-absorbing material 7 on the second inner step 56 inside the inner race 51.

Referring to FIGS. 2, 3, 6, 7 and 9, the liquid perfume diffuser further comprises an outer cap 10. The rotary cover 5 further comprises an annular top flange 59 upwardly extended from an inner side of a top edge 58 thereof. The outer cap 10 is capped on the annular top flange 59 of the rotary cover 5 and stopped at the top edge 58 to block up the rotary cover 5, prohibiting contact between the liquid-absorbing material 7 and the outside open air and avoiding continuously releasing of the liquid perfume.

In application, the user can press the outer cap 10 to force the rotary cover 5 into engagement with the inner cap 3 and drive the outer cap 10 to rotate the rotary cover 5 and the inner cap 3 in direction away from the perfume bottle 1. When wishing to diffuse the liquid perfume into the outside open air, the user can then open the outer cap 10 for enabling the liquid-absorbing material 7 to release the absorbed liquid perfume into the outside open air by the capillary effects Preferably, the bottle stopper 15 further comprises a recycling trough 155, a liquid chamber 157, and a drip hole 1571 located in a bottom side of the liquid chamber 157. The recycling trough 155 is disposed between the liquid guide tube 151 and the bottle stopper 15. The liquid chamber 157 is located at a bottom side of the bottle stopper 15. The recycling trough 155 is disposed in communication with the liquid chamber 157. If the liquid perfume is excessively diffused or the outer cap 10 has never been opened for evaporation of the liquid perfume that has been absorbed by the liquid-absorbing material 7, the overflowed liquid perfume can flow through the recycling trough 155 into the liquid chamber 157 and recycled into the perfume bottle 1 through the drip hole 1571.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A liquid perfume diffuser, comprising:
a perfume bottle holding a liquid perfume therein, said perfume bottle comprising a bottleneck located at a top side thereof, a male thread extended around the periphery of said bottleneck and a bottle stopper fastened to said bottleneck, said bottle stopper comprising a liquid guide tube extended through opposing top and bottom ends thereof, and a fine pore located in a closed bottom end of said liquid guide tube in communication with an opposing top open end of said guide tube;
an inner cap comprising a bottom opening, a top cap head, a protruding tube, a female thread and a plurality of protruding blocks, said protruding tube being axially located at the center of said top cap head and comprising a bottom wall that suspends inside said inner cap and blocks up a bottom end of said protruding tube, a plug downwardly extended from said bottom wall and a liquid guide hole cut through said bottom wall in communication with the inside space of said protruding tube, said protruding blocks being located at a top side of said top cap head and spaced around said protruding tube, said female thread being located on an inside wall of said inner cap for rotatably receiving said male thread of said perfume bottle for enabling said plug to be press-fitted into said liquid guide tube to seal said liquid guide tube and said liquid guide hole;
a rotary cover made in the form of a hollow cylindrical shell member, said rotary cover comprising an inner race and a plurality of notches, said inner race comprising an opening at a free end thereof, said notches being spaced around the said opening of said inner race, said rotary cover being rotatably capped on said inner cap to attach said inner race onto said protruding tube and to force said notches into abutment against the respective said protruding blocks at a top side; and
a liquid-absorbing material mounted in said inner race of said rotary cover in contact with a top side of said protruding tube of said inner cap for absorbing said liquid perfume.

2. The liquid perfume diffuser as claimed in claim 1, wherein each said protruding block of said inner cap comprises a beveled surface located at one side thereof; said rotary cover further comprises a beveled edge located at one side of each said notch of said inner race adapted for mating with the said beveled surfaces of the respective said protruding blocks of said inner cap.

3. The liquid perfume diffuser as claimed in claim 2, wherein said liquid guide tube is an inverted cone tube; said plug is a cone plug.

4. The liquid perfume diffuser as claimed in claim 1, wherein said liquid guide tube is an inverted cone tube; said plug is a cone plug.

5. The liquid perfume diffuser as claimed in claim 1, wherein said inner cap further comprises a stop ring, said stop ring extended around the periphery thereof; said rotary cover further comprises an inner annular flange extended around an inside wall thereof below said inner race and stopped at a bottom side of said stop ring of said inner cap to prohibit said rotary cover from falling out of said inner cap.

6. The liquid perfume diffuser as claimed in claim 5, wherein said inner annular flange defines a beveled surface portion that slopes downwardly inwards toward the inside wall of said rotary cover; said inner cap further comprises a tapered sliding wall downwardly outwardly extended from a bottom side thereof for guiding said beveled surface portion of said inner annular flange to move relative to said inner cap during operation of said rotary cover to force said notches into engagement with the respective said protruding blocks or to carry said notches away from the respective said protruding blocks.

7. The liquid perfume diffuser as claimed in claim 6, wherein said inner cap further comprises a sealing ring sealed to a bottom edge of said tapered sliding wall, said sealing ring comprising a top edge bonded to the said bottom edge of said tapered sliding wall by ultrasonic sealing technology to form a tear line between said tapered sliding wall and said sealing ring, and a plurality of claw portions equiangularly space around an opposing bottom edge thereof and hooked on a bottom side of said male thread of said perfume bottle.

8. The liquid perfume diffuser as claimed in claim 1, wherein said inner cap inner cap further comprises a tooth ring extended around the inside wall thereof below said female thread, said tooth ring comprising a plurality of tooth claws equiangularly spaced around the inside wall of said inner cap for abutment against the periphery of said perfume bottle below said male thread and a gap defined between each two adjacent said tooth claws.

9. The liquid perfume diffuser as claimed in claim 1, further comprising a ring cap mounted in said rotary cover to hold down said liquid-absorbing material in said inner race, wherein said inner race of said rotary cover further comprises a first inner step extended around an inside wall thereof at a top side and a second inner step concentrically spaced below said first inner step; said ring cap comprises a bottom edge stopped at said first inner step of said inner race, and a plurality of axial ribs equiangularly spaced around an inside wall thereof above said bottom edge and stopped at a top side of said liquid-absorbing material to hold down said liquid-absorbing material on said second inner step inside said inner race.

10. The liquid perfume diffuser as claimed in claim 9, wherein said inner race further comprises a plurality of grooves located on and spaced around said second inner step for temporarily accommodating an overflowed amount of said liquid perfume from said liquid-absorbing material.

11. The liquid perfume diffuser as claimed in claim 1, wherein said bottle stopper further comprises a recycling trough disposed between said liquid guide tube and said bottle stopper, a liquid chamber located at a bottom side of said bottle stopper in communication with said recycling trough, and a drip hole located in a bottom side of said liquid chamber.

\* \* \* \* \*